US009763974B2

(12) United States Patent
Traber et al.

(10) Patent No.: US 9,763,974 B2
(45) Date of Patent: *Sep. 19, 2017

(54) GALACTO-RHAMNOGALACTURONATE COMPOSITIONS FOR THE TREATMENT OF DISEASES ASSOCIATED WITH ELEVATED INDUCIBLE NITRIC OXIDE SYNTHASE

(71) Applicant: Galectin Therapeutics, Inc., Duluth, GA (US)

(72) Inventors: Peter G. Traber, Duluth, GA (US); Eliezer Zomer, Newton, MA (US); Anatole A. Klyosov, Newton, MA (US)

(73) Assignee: Galectin Therapeutics, Inc., Norcross, GA (US)

( * ) Notice: Subject to any disclaimer, the term of this patent is extended or adjusted under 35 U.S.C. 154(b) by 72 days.

This patent is subject to a terminal disclaimer.

(21) Appl. No.: 14/405,280

(22) PCT Filed: Jun. 6, 2013

(86) PCT No.: PCT/US2013/044478
§ 371 (c)(1),
(2) Date: Dec. 3, 2014

(87) PCT Pub. No.: WO2013/184892
PCT Pub. Date: Dec. 12, 2013

(65) Prior Publication Data
US 2015/0147338 A1 May 28, 2015

Related U.S. Application Data

(60) Provisional application No. 61/656,288, filed on Jun. 6, 2012.

(51) Int. Cl.
| | | |
|---|---|---|
| *C08B 37/00* | (2006.01) | |
| *C08B 37/06* | (2006.01) | |
| *A61K 31/715* | (2006.01) | |
| *A61K 31/732* | (2006.01) | |
| *A61K 31/738* | (2006.01) | |
| *A61K 45/06* | (2006.01) | |
| *A61K 31/736* | (2006.01) | |

(52) U.S. Cl.
CPC .......... *A61K 31/738* (2013.01); *A61K 31/715* (2013.01); *A61K 31/736* (2013.01); *A61K 45/06* (2013.01)

(58) Field of Classification Search
CPC .... A61K 31/715; A61K 45/06; A61K 31/738; C08B 37/0045; C08B 37/006
USPC ............................. 536/123, 2, 123.1; 514/54
See application file for complete search history.

(56) References Cited

U.S. PATENT DOCUMENTS

| | | |
|---|---|---|
| 2,132,577 A | 10/1938 | Olsen et al. |
| 2,444,266 A | 6/1948 | Maclay et al. |
| 2,503,258 A | 4/1950 | Graham et al. |
| 4,016,351 A | 4/1977 | Eschinasi et al. |
| 4,268,533 A | 5/1981 | Williams et al. |
| 4,686,106 A | 8/1987 | Ehrlich et al. |
| 5,071,970 A | 12/1991 | le Grand et al. |
| 5,434,141 A | 7/1995 | Schafer et al. |
| 5,498,702 A | 3/1996 | Mitchell et al. |
| 5,681,923 A | 10/1997 | Platt |
| 5,760,010 A | 6/1998 | Klein |
| 5,834,442 A | 11/1998 | Raz et al. |
| 5,895,784 A | 4/1999 | Raz et al. |
| 6,297,229 B1 | 10/2001 | Lindor |
| 6,417,173 B1 | 7/2002 | Roufa et al. |
| 6,423,314 B2 | 7/2002 | Platt et al. |
| 6,500,807 B1 | 12/2002 | Platt et al. |
| 6,592,910 B1 | 7/2003 | Banz et al. |
| 6,596,762 B2 | 7/2003 | Sokol |
| 6,632,797 B2 | 10/2003 | Siren |
| 6,680,306 B2 | 1/2004 | Chang et al. |
| 6,756,362 B2 | 6/2004 | Roufa et al. |
| 6,770,622 B2 | 8/2004 | Jarvis et al. |
| 6,890,906 B2 | 5/2005 | Chang et al. |
| 7,018,652 B2 | 3/2006 | Hsia et al. |
| 7,078,064 B2 | 7/2006 | Zabrecky |
| 7,312,208 B2 | 12/2007 | Sasahara et al. |
| 7,491,708 B1 | 2/2009 | Platt et al. |
| 7,732,637 B2 | 6/2010 | Maezono et al. |
| 7,754,745 B2 | 7/2010 | Li et al. |

(Continued)

FOREIGN PATENT DOCUMENTS

| | | |
|---|---|---|
| JP | 2010-229099 A | 10/2010 |
| JP | 2011-505375 A | 2/2011 |

(Continued)

OTHER PUBLICATIONS

International Search Report from International Application No. PCT/US2013/044478 dated Nov. 8, 2013.
Yapo, "Rhamnogalacturonan-I: A Structurally Puzzling and Functionally Versatile Polysaccharide from Plant Cell Walls and Mucilages", Polymer Reviews, Oct. 17, 2011, vol. 51, pp. 391-413.
Ali et al., "Nitric Oxide Augments Mesenchymal Stem Cell Ability to Repair Liver Fibrosis", Journal of Translational Medicine, Apr. 25, 2012, vol. 10, No. 75, pp. 1-9.
Traber et al., Galectin-3 Targeting Drugs Inhibit Multiple Pathological Pathways Leading to Improvement of Non-Alcoholic Steatohepatitis (NASH), 63rd Annual Meeting of the AASLD, Nov. 9, 2012, Hynes Convention Center, Boston, MA.
Dartora et al., "Rhamnogalacturonan from Ilex Paraguariensis: A Potential Adjuvant in Sepsis Treatment" Carbohydrate Polymers, Nov. 12, 2012, vol. 92, Iss. 2, pp. 1776-1782.

(Continued)

*Primary Examiner* — Shaojia Anna Jiang
*Assistant Examiner* — Michael C Henry
(74) *Attorney, Agent, or Firm* — Greenberg Traurig, LLP (57) ABSTRACT

Aspects of the invention provide methods for treatment of a disease associated with elevated iNOS including autoimmune, chronic inflammatory, neurodegenerative, or cardiovascular diseases. In particular, aspects of the invention relate to the use of a therapeutic formulation comprising a galacto-rhamnogalacturonate for the treatment of a disease associated with elevated iNOS including autoimmune, chronic inflammatory, neurodegenerative, or cardiovascular diseases.

14 Claims, 3 Drawing Sheets

(56) References Cited

U.S. PATENT DOCUMENTS

| | | |
|---|---|---|
| 7,846,946 B2 | 12/2010 | Aslanian et al. |
| 7,893,252 B2 | 2/2011 | Platt et al. |
| 7,897,583 B2 | 3/2011 | McKay et al. |
| 7,906,652 B2 | 3/2011 | Baker et al. |
| 7,973,030 B2 | 7/2011 | Sasahara et al. |
| 7,994,226 B2 | 8/2011 | Dohil et al. |
| 7,994,353 B2 | 8/2011 | Oonuki et al. |
| 7,999,107 B2 | 8/2011 | Debenham et al. |
| 8,128,966 B2 | 3/2012 | Staples et al. |
| 8,187,642 B1 | 5/2012 | Staples et al. |
| 8,236,780 B2 | 8/2012 | Platt et al. |
| 8,409,635 B2 | 4/2013 | Staples et al. |
| 8,420,133 B2 | 4/2013 | Staples et al. |
| 8,871,925 B2 | 10/2014 | Zomer et al. |
| 9,200,090 B2 | 12/2015 | Platt et al. |
| 2001/0039048 A1 | 11/2001 | Wu et al. |
| 2002/0155513 A1 | 10/2002 | Hsu et al. |
| 2003/0004132 A1 | 1/2003 | Chang et al. |
| 2003/0013682 A1 | 1/2003 | Banito et al. |
| 2003/0186933 A1 | 10/2003 | Yoo |
| 2004/0023925 A1 | 2/2004 | Chang et al. |
| 2004/0043962 A1 | 3/2004 | Chang et al. |
| 2004/0121981 A1 | 6/2004 | Chang et al. |
| 2004/0223971 A1 | 11/2004 | Chang et al. |
| 2004/0241138 A1 | 12/2004 | Hsu |
| 2005/0008572 A1 | 1/2005 | Prokop et al. |
| 2005/0250735 A1 | 11/2005 | Staples et al. |
| 2006/0094688 A1 | 5/2006 | Tanaka et al. |
| 2006/0211653 A1* | 9/2006 | Ni .................. A61K 9/5063 514/54 |
| 2008/0089959 A1 | 4/2008 | Chang et al. |
| 2008/0107622 A1 | 5/2008 | Platt et al. |
| 2009/0028925 A1 | 1/2009 | Erion et al. |
| 2009/0221533 A1 | 9/2009 | Puder et al. |
| 2011/0008903 A1 | 1/2011 | Paradis et al. |
| 2011/0046086 A1 | 2/2011 | Yun |
| 2011/0082119 A1 | 4/2011 | Yano |
| 2012/0282220 A1 | 11/2012 | Platt et al. |
| 2013/0131010 A1 | 5/2013 | Platt et al. |
| 2013/0261078 A1 | 10/2013 | Zomer et al. |
| 2014/0350238 A1 | 11/2014 | Zomer et al. |
| 2015/0174151 A1 | 6/2015 | Zomer et al. |

FOREIGN PATENT DOCUMENTS

| | | |
|---|---|---|
| WO | 85/05031 A1 | 11/1985 |
| WO | 2005/095463 A1 | 10/2005 |
| WO | 2008/011216 A2 | 1/2008 |
| WO | 2013/040324 A1 | 3/2013 |
| WO | 2013/010134 A2 | 7/2013 |
| WO | 2013/101314 A1 | 7/2013 |
| WO | 2013/184892 A1 | 12/2013 |
| WO | 2014/043708 A1 | 3/2014 |
| WO | 2004/091634 A1 | 10/2014 |

OTHER PUBLICATIONS

Traber et al., "Regression of Fibrosis and Reversal of Cirrhosis in Rats by Galectin Inhibitors in Thioacetamide-Induced Liver Disease", PLOS ONE, Oct. 9, 2013, vol. 8, Iss. 10, pp. 1-12.

Barondes, S.H., et al.: Galectins: a family of animal b-galactoside-binding lectins. Cell 76, 597-598, 1994.

Leffler H. et al. (2004). "Introduction to galectins". Glycoconj. J. 19 (7-9): 433-40.

Wang et al., "Nuclear and cytoplasmic localization of galectin-1 and galectin-3 and their roles in pre-mRNA splicing." in "Galectins" (Klyosov et al eds.), John Wiley and Sons, 87-95 (2008).

Banh et al. "Tumor galectin-1 mediates tumor growth and metastasis through regulation of T-cell apoptosis ," Cancer Res. 71:4423-31 (2011).

Barrow at al., "The role of galectins in colorectal cancer progression," Int. J. Cancer. 129:1-8(2011b).

Cay et al., "Review Immunohistochernical expression of galectin-3 in cancer: a review of the literature," Patoloji Derg. 28(1 ): 1-10 (2012).

Forsman et al., "Galectin 3 aggravates joint inflammation and destruction in antigen-induced arthritis," Arthritis Reum. 63: 445-454 (2011).

Godwin Avwioro,"Histochemical Uses of Haematoxylin—A Review," JPCS. 1:24-34 (2011).

Kolatsi-Joannou et al., "Modified citrus pectin reduces galectin-3 expression and disease severity in experimental acute kidney injury," PLoS One. 6: el8683, doi:l0.137l(journal.pone.00.18683 (2011).

Lefranc et al., "Galectin-1 mediated biochemical controls of melanoma and glioma aggressive behavior," World J. Biol. Chem. 2: 193-201 (2011).

Liu et al., "Galectins in regulation of inflammation and immunity," In Galectins (ed. by Klyosov, A.A., Witzhak, Z.A., and Platt, D.), John Wiley & Sons, Hoboken, New Jersey, pp. 97-113 (2008).

Lopez et al., "Gene expression profiling in lungs of chronic asthmatic mice treated with galectin-3: downregulation of inflammatory and regulator genes," Mediators Inflamm., 823279, Epub 2011 Mar. 20, 2011.

Newlaczyl et aJ., "Galectin-3—a jack-of-all-trades in cancer," Cancer Lett. 313: 123-128 (2011).

Ohshima et al., "Galectin 3 and its binding protein in rheumatoid arthritis," Arthritis Rheum. 48: 2788-2795 (2003).

Sato et al., "Galectins as danger signals in host-pathogen and host-tumor interactions: new members of the growing group of Alarmins." in "Galectins," (Klyosov, et al eds.), John Wiley and Sons, 115-145 (2008).

Toussaint et al., "Galectin-I, a gene preferentially expressed at the tumor margin, promotes glioblastoma cell invasion", Mol Cancer, 11:32. (2012).

Gura, "Science", vol. 278, Nov. 7, 1997, pp. 1041-1042.

Supplementary European Search Report from European Patent Application No. 13800900.6 dated Dec. 23, 2015.

Sun et al., "Structural Characterization of a Tobacco Rhamnogalacturonan", Carbohydrate Polymers 7 (1987) pp. 143-158.

Castano et al., "Serum Amyloid P Inhibits Fibrosis Through FcyR-Dependent Monocyte-Macrophage Regulation in Vivo" Sit Transl Med (2009) vol. 1 No. 5 pp. 1-26.

Duvnjak et al., "Therapy of Nonalcoholic Fatty Liver Disease: Current Status" Journal of Physiology and Pharmacology (2009) vol. 60 Suppl. 7 pp. 57-66.

\* cited by examiner

GALACTO-RHAMNOGALACTURONATE COMPOSITIONS FOR THE TREATMENT OF DISEASES ASSOCIATED WITH ELEVATED INDUCIBLE NITRIC OXIDE SYNTHASE

CROSS-REFERENCE TO RELATED APPLICATIONS

This application is a National Phase application of International Application No. PCT/US2013/044478, filed Jun. 6, 2013, which claims the benefit of and priority to U.S. Provisional Application Ser. No. 61/656,288, filed Jun. 6, 2012, the entire disclosure of each of the foregoing applications are hereby incorporated herein by reference in their entirety.

FIELD OF THE INVENTION

Aspects of the invention relate to methods for treatment of a disease associated with elevated iNOS including autoimmune, chronic inflammatory, neurodegenerative, or cardiovascular diseases.

BACKGROUND OF THE INVENTION

Nitric oxide synthases (NOSs) are a family of enzymes catalyzing the production of nitric oxide (NO) from L-arginine. NO is an important cellular signaling molecule. While nitric oxide has normal physiologic intracellular and extracellular regulatory functions, excessive production of nitric oxide can be in some cases detrimental.

SUMMARY OF THE INVENTION

Aspects of the invention relate to methods of treating a subject having a human disease associated with elevated iNOS activity using a therapeutic composition comprising a galactose-containing polysaccharide compound in an acceptable pharmaceutical carrier for parenteral or enteral administration.

In some embodiments, the galactose-containing polysaccharide compound is a galacto-rhamnogalacturonate. In some embodiments, the galacto-rhamnogalacturonate is a galactoarabino-rhamnogalacturonate.

In some aspects, the invention relate to compositions having a galacto-rhamnogalacturonate compound for the treatment of disease associated with elevated iNOS. Other aspects of the invention relate to the use of a galacto-rhamnogalacturonate compound for the treatment of disease associated with elevated iNOS.

Some aspects of the invention relate to an admixture having a galacto-rhamnogalacturonate and a therapeutic agent. In some embodiments, an admixture having a galacto-rhamnogalacturonate and a therapeutic agent can be used for the treatment or in the manufacture of a pharmaceutical composition for treatment of disease associated with elevated iNOS.

Aspects of the invention relate to the use of a galacto-rhamnogalacturonate in the manufacture of a pharmaceutical composition for treatment of a disease associated with elevated iNOS including autoimmune, chronic inflammatory, neurodegenerative, or cardiovascular diseases.

In some embodiments, the method comprises the steps of obtaining a composition for parenteral or enteral administration comprising a galacto-rhamnogalacturonate compound in an acceptable pharmaceutical carrier and administering to a subject an effective dose of the composition for parenteral administration, the subject having one of the diseases associated with elevated iNOS.

In some embodiments, the effective dose of the composition, when administered in a subject in need thereof, can result in reduction of at least 10% expression of elevated iNOS in the affected tissues of diseases associated with elevated iNOS.

In some embodiments, the effective dose of the composition, when administered in a subject in need thereof, can result in the reduction in the medical consequences of diseases associated with elevated iNOS.

In some embodiments, the compound is a polysaccharide and may be chemically defined as galacto-rhamnogalacturonate. In some embodiments, the galacto-rhamnogalacturonate is a selectively depolymerized, branched heteropolymer having a backbone predominantly comprising 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal).

In some embodiments, the compound is a galactoarabino-rhamnogalacturonate having a backbone predominantly comprising 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5-α-L-arabinose (Ara) residues.

In some embodiments, galactoarabino-rhamnogalacturonate has other side chain minor constituents including xylose (Xyl), glucose (Glu), and fucose (Fuc) or any combination of the foregoing.

In some embodiments, the galactoarabino-rhamnogalacturonate comprises 1,4-β-D-galactose and 1,5-α-L-arabinose residues present in a 2:1 to a 3:1 ratio. In some embodiments, the galactoarabino-rhamnogalacturonate comprises 1,4-β-D-galactose residues, 1,5-α-L-arabinose residues or a combination thereof which represent at least 10 molar percent of the total molar carbohydrates.

In some embodiments, the galacto-rhamnogalacturonate or galactoarabino-rhamnogalacturonate has an average molecular weight ranging from 5 kDa to 55 kDa, from 2 to 20 kDa, from 2 to 65 KDa, from 2 kDa to 80 kDa, from 45 kDa to 65 KDa, or from 20 kDa to 70 kDa.

In some embodiments, the galacto-rhamnogalacturonate compound or the admixture is capable of reducing expression of galectin-3 at the cell surface or substantial decrease in secretion of galectin-3 in the media when used to treat stressed LX2 immortalized human hepatic stellate cells producing galectin-3.

In some embodiments, the galacto-rhamnogalacturonate compound does not induce decreased viability when used to treat LX2 immortalized human hepatic stellate cells. In some embodiments, the galacto-rhamnogalacturonate compound, when utilized to treat LX2 immortalized human hepatic stellate cells in a cell viability assay, does not substantially decrease the viability of activated hepatic stellate cells.

In some embodiments the galacto-rhamnogalacturonate compound is capable of reducing the secretion of TNF alpha cytokine from monocytes or macrophages stressed with endotoxin, for example, by at least 25%. In some embodiments, the galacto-rhamnogalacturonate compound or the admixture does not inhibit cancer cell proliferation in a cancer cell apoptosis or a cytotoxic model, and wherein the compound is not cytotoxic to monocytes/macrophages or activated monocytes/macrophages In some embodiments, the compound does not inhibit cancer cell proliferation in a cancer cell and is not cytotoxic to monocytes or activated monocytes or macrophages at concentrations up to 500 µg/mL.

In some embodiments, the galacto-rhamnogalacturonate can be used in combination with a therapeutically effective amount of a therapeutic agent. In some embodiment, the galacto-rhamnogalacturonate can be used in an admixture.

In some embodiments, the galacto-rhamnogalacturonate can be used in combination with a therapeutically effective amount of cysteamine or a pharmaceutically acceptable salt thereof, or cystamine or a pharmaceutically acceptable salt thereof.

In some embodiments, the galacto-rhamnogalacturonate can be used in combination with a therapeutically effective amount of various anti-oxidant compounds including but not limited to parenteral or oral administration of compositions comprising glycyrrhizin, schisandra, ascorbic acid, L-glutathione, silymarin, lipoic acid, and d-alpha-tocopherol.

In some embodiments, the galacto-rhamnogalacturonate can be used in combination with a therapeutically effective amount of various anti-oxidant compounds including but not limited to parenteral or oral administration of compositions comprising a water soluble Vitamin E preparation, mixed carotenoids, or selenium.

In some embodiments, the galacto-rhamnogalacturonate can be used in combination with a therapeutically effective amount of parenteral or oral administration of lecithin or vitamin B complex.

In some embodiments, the galacto-rhamnogalacturonate can be used in combination with a therapeutically effective amount of bile salt preparations including but not limited to ursodeoxycholic acid, chenodeoxycholic acid of other naturally occurring or synthetic bile acids or bile acid salts.

In some embodiments, the galacto-rhamnogalacturonate can be used in combination with a therapeutically effective amount of antagonists and/or inverse agonists of the Cannabinoid-1 (CB1) receptor.

In some embodiments, the galacto-rhamnogalacturonate can be used in combination with a therapeutically effective amount of a PPAR (peroxisome proliferator-activated receptor) activity regulators.

In some embodiments the galacto-rhamnogalacturonate can be used in combination with a therapeutically effective amount of a benzothiazepine or benzothiepine compound represented by the following formula having a thioamide bond and a quaternary ammonium substituent.

In some embodiments, the galacto-rhamnogalacturonate can be used in combination with a therapeutically effective amount of an RNA antisense construct to inhibit protein tyrosine phosphatase PTPRU.

In some embodiments, the galacto-rhamnogalacturonate can be used in combination with a therapeutically effective amount of a heteroatom-linked substituted piperidine and derivatives thereof useful as histamine H.sub.3 antagonists.

In some embodiments, the galacto-rhamnogalacturonate can be used in combination with a therapeutically effective amount of a azacyclopentane derivative that inhibits stearoyl-coenzyme alpha delta-9 desaturase.

In some embodiments, the galacto-rhamnogalacturonate can be used in combination with a therapeutically effective amount of a acylamide compound having secretagogue or inducer activity of adiponectin.

In some embodiments, the galacto-rhamnogalacturonate can be used in combination with a therapeutically effective amount of quaternary ammonium compounds.

In some embodiments, the galacto-rhamnogalacturonate can be used in combination with a therapeutically effective amount of an isoflavone compound.

In some embodiments, the galacto-rhamnogalacturonate can be used in combination with a therapeutically effective amount of a macrolide antibiotic.

In some embodiments, the galacto-rhamnogalacturonate can be used in combination with a therapeutically effective amount of Glatiramer acetate (also known as Copolymer 1, Cop-1, or Copaxone—as marketed by Teva Pharmaceuticals), an immunomodulator drug currently used to treat multiple sclerosis.

In some embodiments, the galacto-rhamnogalacturonate can be used in combination with a therapeutically effective amount of pentraxin proteins, including but not limited to recombinant pentraxin-2.

In some embodiments, the galacto-rhamnogalacturonate v in combination with a therapeutically effective amount of a stain, for example but not limited to HMG-CoA reductase inhibitors such as atorvastatin and simvastatin.

In some embodiments, the galacto-rhamnogalacturonate v in combination with a therapeutically effective amount of an n-acetyl cysteine, In some embodiments, the galacto-rhamnogalacturonate can be used in combination with a therapeutically effective amount of another galectin inhibitor that may inhibit single galectin proteins or a set of galectin proteins including but not limited small organic inhibitors of galectin, monoclonal antibodies, RNA inhibitors, small binding peptides, or protein inhibitors.

In some embodiments, the galacto-rhamnogalacturonate can be used in combination with a therapeutically effective amount of a monoclonal antibody to inhibit lysyl oxidase (or other like enzymes that crosslink collagen), or a monoclonal antibody to connective tissue growth factor.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting. It is understood that aspects and embodiments of the invention described herein include "consisting" and/or "consisting essentially of" aspects and embodiments.

Unless otherwise specified, all percentages expressed herein are weight/weight.

Nitric oxide synthases (NOSs) are a family of enzymes catalyzing the production of nitric oxide (NO) from L-arginine. NO is an important cellular signaling molecule. Three principal isoforms of this enzyme have been isolated and characterized, each associated with different physiological functions: the immune response (inducible NOS or iNOS), smooth muscle relaxation (endothelial NOS or eNOS), and neuronal signaling (neuronal NOS or nNOS). The inducible isoform, iNOS, is involved in immune response, binds calmodulin at physiologically relevant concentrations, and produces NO as an immune defense mechanism, as NO is a free radical with an unpaired electron. It is the proximate cause of septic shock and may function in autoimmune disease. In addition, an increase in the expression of iNOS has been shown to be important in multiple human diseases including infectious diseases, autoimmune and chronic inflammatory diseases, neurodegenerative diseases, and cardiovascular disease.

Aspects of the invention relate to a method for reducing iNOS expression which has potential for treatment in these human disorders.

iNOS induction can be involved in the pathogenesis of many human diseases.

For example, iNOS has been shown to be the proximate cause of septic shock. NO production by iNOS contributes to excessive vasodilation during endotoxic (septic) and cytokine-induced shock.

Increase in the expression of iNOS has been shown to be associated with autoimmune and chronic inflammatory diseases including but not limited to rheumatoid arthritis, multiple sclerosis, Sjogren's syndrome, Asthma, bronchiectasis, idiopathic pulmonary fibrosis, ulcerative colitis, Crohn's disease, necrotizing enterocolitis, celiac disease, glomerulonephropathies and other kidney inflammatory disease, chronic inflammatory liver disease (viral, alcoholic, steatohepatitis, biliary, autoimmune), psoriasis, cutaneous and systemic lupus erythematosis, systemic sclerosis, dermatitis, and periapical periodontitis.

Increase in the expression of iNOS has been shown to be associated with neurodegenerative diseases including but not limited to Alzheimer's disease and Parkinson's disease, Increase in the expression of iNOS has been shown to be associated with cardiovascular diseases including but not limited to myocarditis, dilated cardiomyopathy and heart failure, cardiac allograft rejection, atherosclerosis, and pulmonary arterial hypertension.

Increase in the expression of iNOS has been shown to be associated with the biology of cancer and is expressed in a wide variety of tumors.

iNOS may be involved in human diseases through expression in multiple cell types, including but not limited to, epithelial cells, stromal cells, endothelial cells, macrophages, and multiple types of immune cells.

In some embodiments, one mechanism by which galactorhamnogalacturonate or a galactoarabino-rhamnogalacturonate may reduce the expression of iNOS is through binding to galectin proteins.

Galectins (also known as galaptins or S-lectin) are a family of lectins which bind beta-galactoside. Galectin as general name was proposed in 1994 for a family of animal lectins (Barondes, S. H., et al.: Galectins: a family of animal b-galactoside-binding lectins. Cell 76, 597-598, 1994), The family is defined by having at least one characteristic carbohydrate recognition domain (CRD) with an affinity for beta-galactosides and sharing certain sequence elements. Within the same peptide chain, some galectins have a CRD with only a few additional amino acids, whereas others have two CRDs joined by a link peptide, and one (galectin-3) has one CRD joined to a different type of domain. The galectin carbohydrate recognition domain (CRD) is a beta-sandwich of about 135 amino acids. The two sheets are slightly bent with 6 strands forming the concave side and 5 strands forming the convex side. The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, e.g., development, differentiation, morphogenesis, tumor metastasis, apoptosis, RNA splicing, etc. However, relatively little is known about the mechanism by which galectins exert these functions, particularly in terms of carbohydrate recognition.

Generally, the carbohydrate domain binds to galactose residues associated with glycoproteins. At least fifteen mammalian galectin proteins have been identified which have one or two carbohydrate domain in tandem.

Each galectin protein has a galactose binding domain and other domains that allow homo- or hetero-dimerization to other galectin proteins. Galectin proteins are expressed in a broad range of cells and tissues at low levels under physiological conditions and are found in the nucleus, cytoplasm, and are secreted into the extracellular space by a non-traditional secretory pathway.

The galactose binding domain of galectins binds to galactose containing glycoproteins located on the cell surface or on extracellular matrix proteins. The dimerization domains on galectins promote interaction of galectin proteins, thereby creating interaction between membrane or matrix glycoproteins. These interactions promote cell-cell, cell-matrix, and matrix-matrix interactions and association of membrane receptors that can cause activation, inactivation, or modulation of cell receptor activity leading to modulation of intracellular signaling and subsequent events.

Certain galectin proteins are markedly up-regulated and secreted in high amounts from cells in pathological situations. Multiple inflammatory cells, including but not limited to macrophages and lymphocytes, in tissue inflammation states and repair (fibrosis, scarring) express galectins, particularly galectin-1 and galectin-3.

A "subject" to be treated can mean either a human or a non-human subject.

The term "effective dose" means the amount of galacto-rhamnogalacturonate or other agent in combination with galacto-rhamnogalacturonate that, when administered as a parental dose or in an oral formulation to an animal or human with a disease associated with elevated iNOS, is capable of reducing iNOS expression by at least 10% in the disease affected tissue.

An effective amount of galactose containing polysaccharide administered to a human subject can be within the range of 0.5 mg/kg up to 25 mg/kg body weight, or 1 mg/kg, or 2 mg/kg, or 5 mg/kg, or 7.5 mg/kg, or 10 mg/kg body weight, or 15 mg/kg body weight.

In some aspects, methods for treating (e.g., controlling, relieving, ameliorating, alleviating, or slowing the progression of) or methods for preventing (e.g., delaying the onset of or reducing the risk of developing) one or more diseases, disorders, or conditions in which iNOS is involved, in a subject in need thereof are featured. The methods include administering to the subject an effective amount of a galacto-rhamnogalacturonate compound, or a composition comprising the galacto-rhamnogalacturonate compound, to a subject having one of a number of diseases associated with elevated iNOS levels.

The term "pharmaceutically acceptable carrier" refers to any and all solvents, dispersion media, e.g., human albumin or cross-linked gelatin polypeptides, coatings, antibacterial and antifungal compounds, isotonic, e.g., sodium chloride or sodium glutamate, and absorption delaying compounds, and the like that are physiologically compatible. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

The term "efficacy" refers in some embodiments to demonstrating an improvement in the iNOS associated disease including but not limited to reduced end-organ damage or improvement in signs and symptoms of the disease.

Aspects of the invention relate to methods of treating a subject having a human disease associated with elevated iNOS activity using a therapeutic composition comprising a galactose-containing polysaccharide compound in an acceptable pharmaceutical carrier for parenteral or enteral administration.

In some embodiments, the method of treating comprises the step of obtaining a composition for parenteral or enteral administration comprising a compound in an acceptable pharmaceutical carrier.

In some aspects, the invention relate to compositions having a galacto-rhamnogalacturonate compound for the treatment of disease associated with elevated iNOS. In some embodiments, the composition is an admixture having a galacto-rhamnogalacturonate and a therapeutic agent. The term "admixture" means more than one component mixed together to form a combination. For purposes of the present invention, "admixture" means the mixture of two or more compounds at any time prior or subsequent to, or concomitant with, administration.

Some aspects of the invention relate to the use of a galacto-rhamnogalacturonate compound for the treatment of disease associated with elevated iNOS. In some embodiments, an admixture having a galacto-rhamnogalacturonate and a therapeutic agent can be used for the treatment or in the manufacture of a pharmaceutical composition for treatment of disease associated with elevated iNOS.

In some embodiments the galacto-rhamnogalacturonate compound can be produced by the method described in U.S. Pat. No. 8,236,780 and in U.S. application Ser. No. 13/573,442, and in International Patent Application No. PCT/US12/55311 entitled "Compositions of novel carbohydrate drug for the treatment of human diseases", and incorporated expressly by reference in their entirety for all purposes.

In some embodiments, the galacto-rhamnogalacturonan compound can be substantially free of microbial endotoxin, agricultural pesticides, agricultural herbicides, copper, heavy metals, proteins, nitrogenous compounds or any combination of the foregoing. By "substantially free", it is meant that the composition contain less than 5%, less than 2%, less than 1%, less than 0.5% by weight.

In some embodiments, the galacto-rhamnogalacturonan compound does not induce decreased viability when used to treat LX2 immortalized human hepatic stellate cells in a cell viability assay. For example, the galacto-rhamnogalacturonan compound does not induce decreased viability when used to treat LX2 immortalized human hepatic stellate cells when used at concentrations up to 500 µg/mL.

In some embodiments, the galacto-rhamnogalacturonan compound is capable of inducing substantial decrease in expression of galectin-3 at the cell surface or substantial decrease in secretion of galectin-3 in the media when used to treat stressed LX2 immortalized human hepatic stellate cells producing galectin-3.

In some embodiments the galacto-rhamnogalacturonan compound is capable of reducing the secretion of TNF alpha cytokine from monocytes stressed with endotoxin. In some embodiments, the galacto-rhamnogalacturonan compound is capable of reducing the secretion of TNF alpha by the activated monocytes or the activated macrophages by at least 25%.

In some embodiments the galacto-rhamnogalacturonan compound does not inhibit cancer cell proliferation in a cancer cell apoptosis or a cytotoxic model. In some embodiments the galacto-rhamnogalacturonan compound is not cytotoxic to monocytes/macrophages or activated monocytes/macrophages.

In some embodiments, the compound does not inhibit cancer cell proliferation in a cancer cell and is not cytotoxic to monocytes/macrophages or activated monocytes/macrophages at concentrations up to 500 µg/mL.

In some embodiments, the compound is a polysaccharide and may be chemically defined as a subtype of galacto-rhamnogalacturonate termed galactoarabino-rhamnogalacturonate (GA-RG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5-α-L arabinose (Ara) residues or combination thereof. Other side chain minor constituents may include xylose (Xyl), glucose (Glu), and fucose (Fuc).

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments the compound can be produced by a process comprising depolymerization catabolized by targeted peroxidation cleavage of glycosidic bonds by ionized OH sup-generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

In some embodiments, the depolymerized compound can be exposed to pH of between 8 to 10, for 10 to 30 minutes at temperature of 2 to 60° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (e.g. at temperatures ranging from 30 to 80° C.) to remove any residual endotoxin, copper and heavy metals, agricultural contaminates and other impurities.

In some embodiments, the compound is a polysaccharide chemically defined as galacto-rhamnogalacturonate or galactoarabino-rhamnogalacturonate, a branched heteropolymer with average molecular weight distribution of 2,000 to 80,000 Da, or 20,000 to 70,000 Da, 2,000 to 65,000 Da, or 45,000 to 65,000 Da, or 2,000-20,000 Da or 5,000 to 55,000 Daltons, as determined by SEC-RI and/or the SEC-MALLS methods.

In some embodiments, the molar percent of 1,5-α-L-Ara residues in the compound of the present invention may be zero or only found in trace amounts of up to 1%.

In some embodiments, the compound is a galactoarabino-rhamnogalacturonate having a molar percent of the 1,4-β-D-Gal and 1,5-α-L-Ara residues that can exceed 10% of the total molar carbohydrates with approximate ratio ranging from 1:1 to 3:1 respectively.

In some embodiments, the compound can be a highly soluble modified polysaccharide sufficiently reduced in molecular weight range, so as to be compatible with therapeutic formulations for pluralistic administration via routes including but not limited to intravenous, subcutaneous, intra-articular, inhaled, and oral. For example, the compound can be from about for example from about 2,000 to about 80,000 Da, or for example from about 2,000 to about 65,000 Da or for example from about 20,000 to 70,000 Da, or for example from about 45,000 to 65,000 Da, or for example from about 2,000 to 20,000 Da or for example from about 5,000 to 45,000 Da.

In some embodiments, the 1,4-linked galacturonic acid and the methyl galacturonate residues backbone can represent between 55 to 85 molar percent of the total carbohydrate molar content, the branched heteropolymer of alternating α-1,2 linked rhamnose and α-1,4-linked GalA residues can represent between 1 and 3 molar percent of the total carbohydrate molar content, the oligomer 1,4-β-D-galactose of the primary branching can represent between 6 to 15 molar percent of the total carbohydrate molar content and the oligomer 1,5-α-L-arabinose of the primary branching can represent between 2 to 8 molar percent of the total carbohydrate molar content, as characterized by gas chromatography/mass spectrometry.

In some embodiments, the 1,4-β-D-galactose residues, 1,5-α-L-arabinose residues or combination thereof can represent at least 8 molar percent of the total carbohydrate molar content.

In some embodiments, the 1,4-β-D-galactose and 1,5-α-L-arabinose residues can be present in a 2:1 ratio.

In some embodiments, the compound can have a degree of methoxylation ranging from 40% to 70% out of maximum 87%.

In some embodiments, the compound can have a methyl galacturonate to galacturonic acid ratio ranging from 2:1 to 1:2.

In some embodiments, the compound can have a methyl galacturonate plus galacturonic acid ratio to galactose ranging from 4:1 to 8:1.

In some embodiments, the compound is a polysaccharide and may be chemically defined as galacto-rhamnogalacturonate (GR), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal). Other side chain minor constituents may include arabinose (Ara), xylose (Xyl), glucose (Glu), and fucose (Fuc).

In some embodiments, the compound can be synthesized from natural, highly branched, minimally processed and high methoxylated USP pectin which may come from any plant sources, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments the compound can be produced by a process comprising depolymerization catabolized by targeted peroxidation cleavage of glycosidic bonds by ionized OH sup-generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

In some embodiments, the depolymerized compound can be exposed to pH of between 8 to 10 for 10 to 30 minutes at temperature of 2 to 30° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (50-65° C.) to remove any residual endotoxin, copper and heavy metals, agricultural contaminates and other impurities.

In some embodiments, soluble chemically altered galacto-rhamnogalacturonates are prepared by modifying naturally occurring polymers to reduce the molecular weight for the desired range, reducing the alkylated group (demethoxylation or deacetylation). Prior to chemical modification, the natural polysaccharides may have a molecular weight range of between about 40,000-1,000,000 Da with multiple branches of saccharides, for example, branches comprised of 1 to 20 monosaccharides of glucose, arabinose, galactose etc, and these branches may be connected to the backbone via neutral monosaccharides such as rhamnose. These molecules may further include a single or chain of uronic acid saccharide backbone that may be esterified from as little as about 2% to as much as about 70%. The multiple branches themselves may have multiple branches of saccharides, the multiple branches optionally including neutral saccharides and neutral saccharide derivatives creating mainly hydrophobic entities.

In some embodiments, the galacto-rhamnogalacturonate composition may be produced by various treatments, including heat, high or low pH, various forms of molecular weight exclusion filtration (or combinations of these methods) using raw pectin material from any plant source including but not limited to apple, citrus, or beet pectin, some of which are available commercially as USP pectin material.

In some embodiments, the compound falls within the general class comprising a substantially demethoxylated polygalacturonic acid backbone having rhamnose residues pendent therefrom. It is believed that in materials of this type, the terminal galactose units pendent from the backbone bind to galectin proteins. The remaining bulk of the molecule can potentiate the compound's action in moderating immune system response. While not wishing to be bound by speculation, the remaining bulk of the molecule may either interact with remaining portions of the galectin protein and/or may prolong the binding of the sugar portion thereto.

While the foregoing discussion has been primarily directed to therapeutic materials based upon modified pectins, it is to be understood that the present invention is not so limited. In accord with the general principles of the present invention, any member of the broad class of compounds which can interact with and block galectins may be employed. These materials, in an embodiment, comprise carbohydrate materials, since such materials are low in toxicity and exhibit strong interaction with galectins or exhibit a strong anti-inflammatory effect. Modified pectin materials comprise one particularly group of carbohydrate materials. Likewise, synthetic and semi-synthetic analogs thereof such as polygalacturonic acid materials may be similarly employed.

Yet another class of materials of the present invention comprises molecules which have a first portion, which is typically a carbohydrate, and which is capable of binding to galectins, joined to a second portion which inactivates or otherwise moderates the activity of a protein. This second portion need not be a carbohydrate and can comprise a material which cross links or otherwise denatures the segment of protein comprising an active portion of the galectin protein, or an active portion of another protein which interacts with the galectin. Such materials include active species such as sulfur or other chalcogen elements alone or in combination such as thiols, sulfhydryls and the like. Other active species may comprise cyano groups, thiocyanates, alkylating agents, aldehydes and the like. Some active species may be proteins including but not limited to monoclonal antibodies.

An effective dose of the compound of the present invention or a composition comprising an effective dose of the compound can be administered via a variety of routes including, parenteral via an intravenous infusion given as repeated bolus infusions or constant infusion, intradermal injection, subcutaneously given as repeated bolus injection or constant infusion, intra-articular injection, inhaled in an appropriate formulation, or oral administration.

The amount administered depends on the compound formulation, route of administration, etc. and is generally empirically determined in routine trials, and variations will necessarily occur depending on the target, the host, and the route of administration, etc.

"Administration" refers to oral, or parenteral including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection and infusion.

In some embodiments, the therapeutic compositions may be administered orally, by intravenous injection, by subcutaneous injection or by infusion.

An effective parental dose may be given daily (in one or divided doses), three times weekly, two times weekly, or monthly via intravenous, intradermal, subcutaneous or other routes as practiced by the medical professional to administrate drugs.

In some embodiments, an effective dose of a galacto-rhamnogalacturonate can be administered in a formulation for oral administration. The formulation may include methods of physical alterations of the compound or additions of various agents that enhance the oral absorption of the galactose-containing polysaccharide. An effective oral dose could be 10 times and up to 100 times the amount of the effective parental dose. An effective oral dose may be given daily, in one or divided doses or twice, three times weekly, or monthly.

In some embodiments, the galacto-rhamnogalacturonate compounds described herein can be co-administered with one or more other therapeutic agents. In certain embodiments, the additional agents may be administered separately, as part of a multiple dose regimen, from the compounds of this invention (e.g., sequentially, e.g., on different overlapping schedules with the administration of the compound of the invention. In other embodiments, these agents may be part of a single dosage form, mixed together with the compounds of this invention in a single composition. In still another embodiment, these agents can be given as a separate dose that is administered at about the same time that the compound of the invention.

In some embodiment, the galacto-rhamnogalacturonate can be used in admixture.

When the compositions include a combination of the galacto-rhamnogalacturonate compounds and one or more additional therapeutic or prophylactic agents, both the compound and the additional agent can be present at dosage levels of between about 1 to 100%, and more preferably between about 5 to 95% of the dosage normally administered in a monotherapy regimen.

In some embodiments, the compound is a galacto-rhamnogalacturonate and can be used in combination with a therapeutically effective amount of cysteamine or a pharmaceutically acceptable salt thereof, or cystamine or a pharmaceutically acceptable salt thereof. [see U.S. Pat. No. 7,994,226, incorporated expressly by reference for all purposes.]

In some embodiments, the compound is a galacto-rhamnogalacturonate and can be used in combination with a therapeutically effective amount of various anti-oxidant compounds including but not limited to parenteral or oral administration of compositions comprising glycyrrhizin, schisandra, ascorbic acid, L-glutathione, silymarin, lipoic acid, and d-alpha-tocopherol. [see U.S. Pat. No. 7,078,064, incorporated expressly by reference for all purposes.]

In some embodiments, the compound is a galacto-rhamnogalacturonate and can be used in combination with a therapeutically effective amount of various anti-oxidant compounds including but not limited to parenteral or oral administration of compositions comprising a water soluble Vitamin E preparation, mixed carotenoids, or selenium [see U.S. Pat. No. 6,596,762, incorporated expressly by reference for all purposes.]

In some embodiments, the compound is a galacto-rhamnogalacturonate and can be used in combination with a therapeutically effective amount of parenteral or oral administration of lecithin or vitamin B complex [see U.S. Pat. Nos. 7,018,652; 6,180,139, incorporated expressly by reference for all purposes.]

In some embodiments, the compound is a galacto-rhamnogalacturonate and can be used in combination with a therapeutically effective amount of bile salt preparations including but not limited to ursodeoxycholic acid, chenodeoxycholic acid of other naturally occurring or synthetic bile acids or bile acid salts. [see U.S. Pat. No. 6,297,229, incorporated expressly by reference for all purposes.]

In some embodiments, the compound is a galacto-rhamnogalacturonate and can be used in combination with a therapeutically effective amount of antagonists and/or inverse agonists of the Cannabinoid-1 (CB1) receptor. [see U.S. Pat. Nos. 7,999,107; 7,906,652, incorporated expressly by reference for all purposes.]

In some embodiments, the compound is a galacto-rhamnogalacturonate and can be used in combination with a therapeutically effective amount of PPAR (peroxisome proliferator-activated receptor) activity regulators. [see U.S. Pat. No. 7,994,353, incorporated expressly by reference for all purposes.]

In some embodiments, the compound is a galacto-rhamnogalacturonate and can be used in combination with a therapeutically effective amount of a benzothiazepine or benzothiepine compound represented by the following formula having a thioamide bond and a quaternary ammonium substituent. [see U.S. Pat. No. 7,973,030, incorporated expressly by reference for all purposes.]

In some embodiments, the compound is a galacto-rhamnogalacturonate and can be used in combination with a therapeutically effective amount of an RNA antisense construct to inhibit protein tyrosine phosphatase PTPRU. [see U.S. Pat. No. 7,897,583, incorporated expressly by reference for all purposes.]

In some embodiments, the compound is a galacto-rhamnogalacturonate and can be used in combination with a therapeutically effective amount of a heteroatom-linked substituted piperidine and derivatives thereof useful as histamine H.sub.3 antagonists. [see U.S. Pat. No. 7,846,946, incorporated expressly by reference for all purposes.]

In some embodiments, the compound is a galacto-rhamnogalacturonate and can be used in combination with a therapeutically effective amount of a azacyclopentane derivative that inhibits stearoyl-coenzyme alpha delta-9 desaturase. [see U.S. Pat. No. 7,754,745, incorporated expressly by reference for all purposes.]

In some embodiments, the compound is a galacto-rhamnogalacturonate and can be used in combination with a therapeutically effective amount of a acylamide compound having secretagogue or inducer activity of adiponectin. [see U.S. Pat. No. 7,732,637, incorporated expressly by reference for all purposes.]

In some embodiments, the compound is a galacto-rhamnogalacturonate and can be used in combination with a therapeutically effective amount of quaternary ammonium compounds. [see U.S. Pat. No. 7,312,208, incorporated expressly by reference for all purposes.]

In some embodiments, the compound is a galacto-rhamnogalacturonate and can be used in combination with a therapeutically effective amount of a isoflavone compound. [see U.S. Pat. No. 6,592,910, incorporated expressly by reference for all purposes.]

In some embodiments, the compound is a galacto-rhamnogalacturonate and can be used in combination with a therapeutically effective amount of a macrolide antibiotic. [see U.S. Pat. No. 5,760,010, incorporated expressly by reference for all purposes.]

In some embodiments, the compound is a galacto-rhamnogalacturonate and can be used in combination with a therapeutically effective amount of Glatiramer acetate (also known as Copolymer 1, Cop-1, or Copaxone—as marketed by Teva Pharmaceuticals), an immunomodulator drug currently used to treat multiple sclerosis.

In some embodiments, the compound is galacto-rhamnogalacturonate and can be used in combination with a therapeutically effective amount of a stain, for example but not limited to HMG-CoA reductase inhibitors such as atorvastatin and simvastatin.

In some embodiments, the compound is a galacto-rhamnogalacturonate and can be used in combination with a therapeutically effective amount of an n-acetyl cysteine.

In some embodiments, the compound is a galacto-rhamnogalacturonate and can be used in combination with a therapeutically effective amount of another galectin inhibitor that may inhibit single galectin proteins or a set of galectin proteins including but not limited small organic inhibitors of galectin, monoclonal antibodies, RNA inhibitors, small binding peptides, or protein inhibitors.

In some embodiments, the compound is a galacto-rhamnogalacturonate and can be used in combination with a therapeutically effective amount of a monoclonal antibody to inhibit lysyl oxidase or monoclonal antibody that binds to connective tissue growth factor.

In another embodiment, the compound is a galacto-rhamnogalacturonate and can be used in combination with a therapeutically effective amount of pentraxin proteins, including but not limited to recombinant pentraxin-2.

In some embodiments, an effective dose of galactose-containing polysaccharide can be administered via a variety of routes including, parenteral via an intravenous infusion given as repeated bolus infusions or constant infusion, intradermal injection, subcutaneously given as repeated bolus injection or constant infusion, or oral administration.

An effective parental dose (given intravenously, intraperitoneally, or subcutaneously) of galactose containing polysaccharide to an experimental animal is within the range of 2 mg/kg up to 160 mg/kg body weight, or 10 mg/kg, or 30 mg/kg, or 60 mg/kg, or 90 mg/kg, or 120 mg/kg body weight.

An effective parenteral dose (given intravenously, intraperitoneally, or subcutaneously) of galactose containing polysaccharide to an experimental animal can be administered three times weekly, twice weekly, once weekly, once every two weeks, once monthly, or as a constant infusion.

An effective parental dose (given intravenously or subcutaneously) of galactose containing polysaccharide to a human subject is within the range of 0.5 mg/kg up to 25 mg/kg body weight, or 1 mg/kg, or 2 mg/kg, or 5 mg/kg, or 7.5 mg/kg, or 10 mg/kg body weight, or 15 mg/kg body weight.

An effective parenteral dose (given intravenously or subcutaneously) of galactose containing polysaccharide to a human subject can be administered three times weekly, twice weekly, once weekly, once every two weeks, once monthly, or as a constant infusion.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the present invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, a therapeutically effective dose can be evaluated by a change of at least 10% in the level of the serum biomarkers of the iNOS associated disease.

In some embodiments, a therapeutically effective dose can be evaluated by a reduction of at least 10% in the level of galectin-3 in liver tissue or serum.

In some embodiments, a therapeutically effective dose can be evaluated by a change in the level of galectin-3 in serum.

The present invention will be further described in the following examples. It should be understood that these examples are for illustrative purposes only and are not to be construed as limiting the present invention in any manner.

EXAMPLE 1

Method of Manufacturing
Galacto-Rhamnogalacturonate Compound

The following is merely an illustrative example of the production of a therapeutic polysaccharide that is not meant to limit the invention. In this case, the galacto-rhamnogalacturonate produced has been labeled GR-MD-02 in this application.

Apple pectin USP HM (50 kg) was dissolved and heated in water to 35-85° C. 1 M HCl or NaOH was added in order to pH-adjust the solution to pH 5-7 and mixed well. The mixing was continued for 2 hours at the 35-85° C. set point. 1M NaOH or HCl was added as needed to readjust pH to between 5 and 7. Solution was cooled to 30° C. At 30° C., pH was adjusted to between 5 and 7.

$CuSO_4$ is added to the pH-adjusted pectin solution so as to result in a final 1 mM $CuSO_4$ concentration. The 1 mM $CuSO_4$ solution was mixed for 30 minutes at a temperature of between 10° C. and 30° C.

At the conclusion of the 30 minute, 1 mM $CuSO_4$ mixing step, 50 grams sodium ascorbate was added (amount was pre-calibrated to achieve the desired MW) and mixed for 5 to 20 minutes. $H_2O_2$ was added start with 0.02 and up to 1.0 moles/kg pectin (pre-calibrated for initial starting pectin MW) and the $H_2O_2$ concentration was maintained for 4 hours (using quantitative test, Sigma, St-Louis) while the solution pH was maintained between 4 and 7.

5M NaOH was added to the solution so as to result in a solution pH of between 8 and 10. The pH-adjusted solution was mixed for 10-30 minutes. Concentrated HCL was then added to the pH-adjusted solution to adjust the pH of the solution to between 4 and 5. The solution, once adjusted to pH between 4 and 5 can be kept mixing for 2 to 24 hours between 2° C. and 8° C.

Solution was then heated to 80° C. for 30-180 minutes and 1-5 kg of Filter-Aid was added (Celite) to the solution, and the solution with added Celite was stirred for 30 minutes and then filtered. The solids resulting from the filtration were discarded.

The filtrate was concentrated 1.5-3× under vacuum, and then pH-adjusted to between 3 and 5. Hot ethanol or isopropanol was added on a 50% weight. The mixture was stirred 1-2 hours to precipitate product, and the mixture was then filtered. The filtrate was discarded, leaving a white to off-white precipitate.

Cold 96% EtOH was added to the solution and the resulting slurry was then stirred for 30 minutes. The solution was filtered and the filtrate was discarded. The 96% EtOH slurry step was repeated, followed by a final filtration and recovery of the white to off-white precipitate.

EXAMPLE 2

Method of Treatment that Reduces iNOS in a Mouse Model of Steatohepatitis

The experimental model used in this example is the mouse in which diabetes was induced and a high fat diet was administered, a model that has been called STAM mice. Diabetes is induced immediately following birth with a single injection of streptozotocin and then four weeks later the mice are started on a high fat diet. This is a proven chronic inflammatory model in which the mice consistently develop steatohepatitis with hepatocyte fat accumulation, evidence of hepatocyte toxicity, portal and lobular inflammatory infiltrates, peri-sinusoidal fibrosis, advanced fibrosis with nodule formation, cirrhosis, and ultimately hepatocellular carcinoma in a certain percentage of animals.

GR-MD-02, produced as described in Example 1, was given in a dose of 60 mg/kg twice weekly intravenously for four (4) weeks starting at week 9 after initiation of the model through week 12.

Figure 1A:
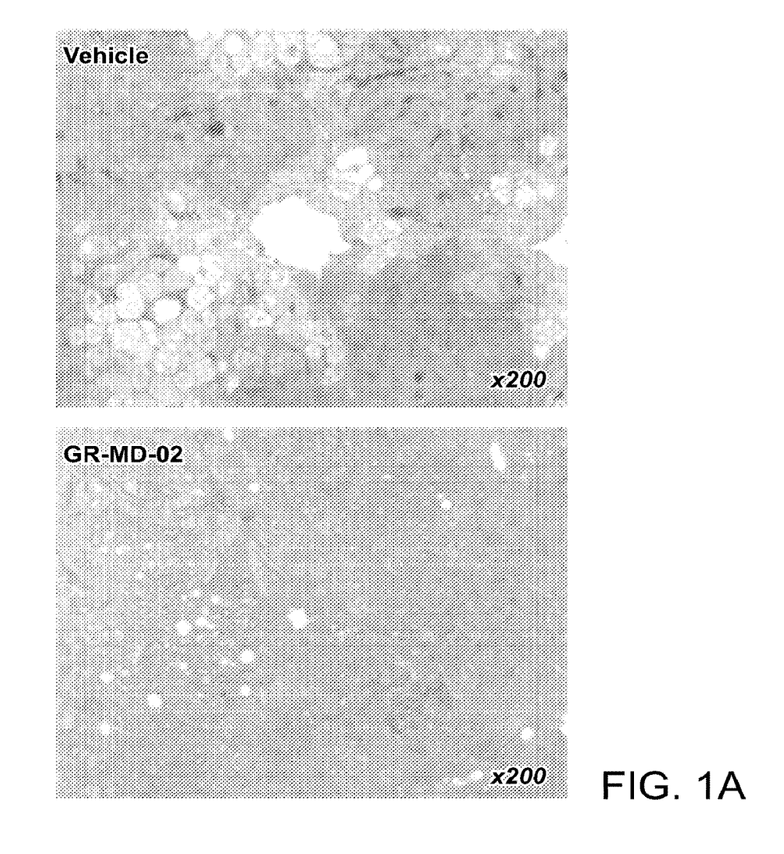
FIG. 1A shows of inducible nitric oxide synthase (iNOS) in liver tissue of experimental groups according to one embodiment.
Figure 1B:
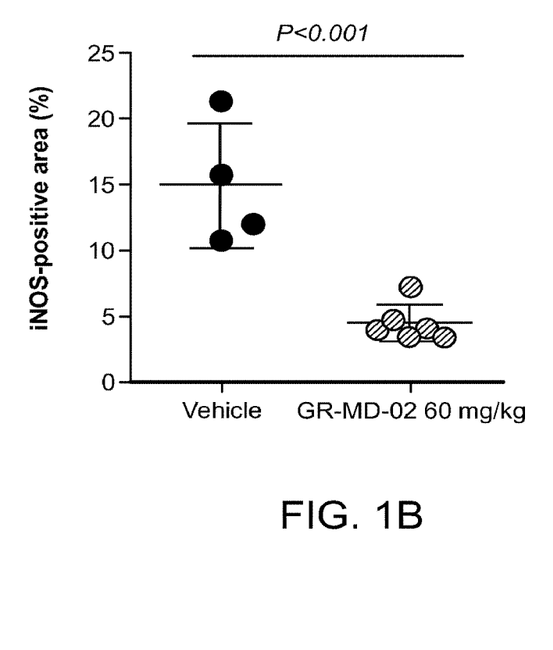
FIG. 1B shows digital morphometry of inducible nitric oxide synthase (iNOS) in liver tissue of experimental groups according to one embodiment.

FIG. 1A shows that the amount of iNOS detected in liver tissue was elevated in the vehicle-treated control livers over normal animals and markedly reduced upon treatment with GR-MD-02. FIG. 1B shows the quantification of iNOS immunoreactivity which indicates that treatment with GR-MD-02 results in a statistically significant reduction of iNOS immunoreactivity.

GR-MD-02, produced as described in Example 1, was also given in a dose of 120 mg/kg, 60 mg/kg, 30 mg/kg, 10 mg/kg once weekly intravenously for six weeks at the each of the starting at week six of the model and ending at week 12.

Figure 2:
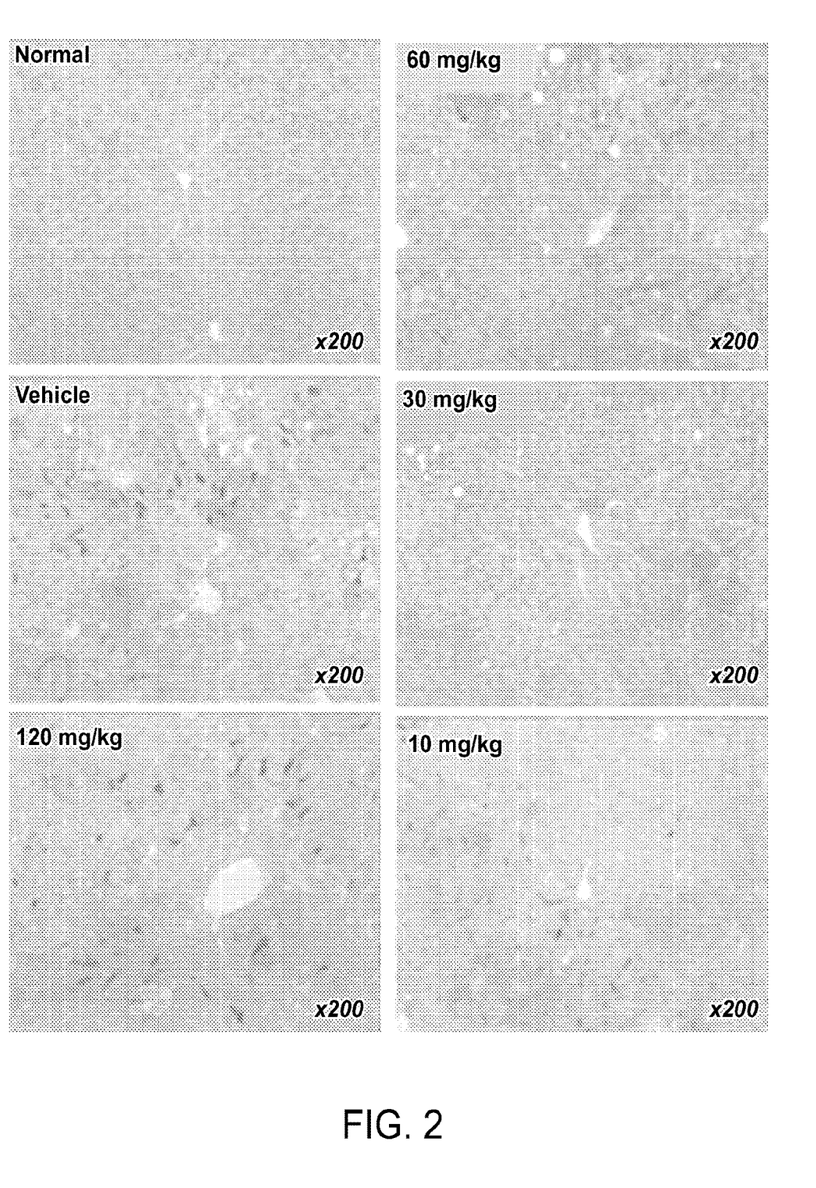
FIG. 2 shows immunohistochemical staning of inducible nitric oxide synthase (iNOS) in liver tissue of experimental groups according to one embodiment.
Figure 3:
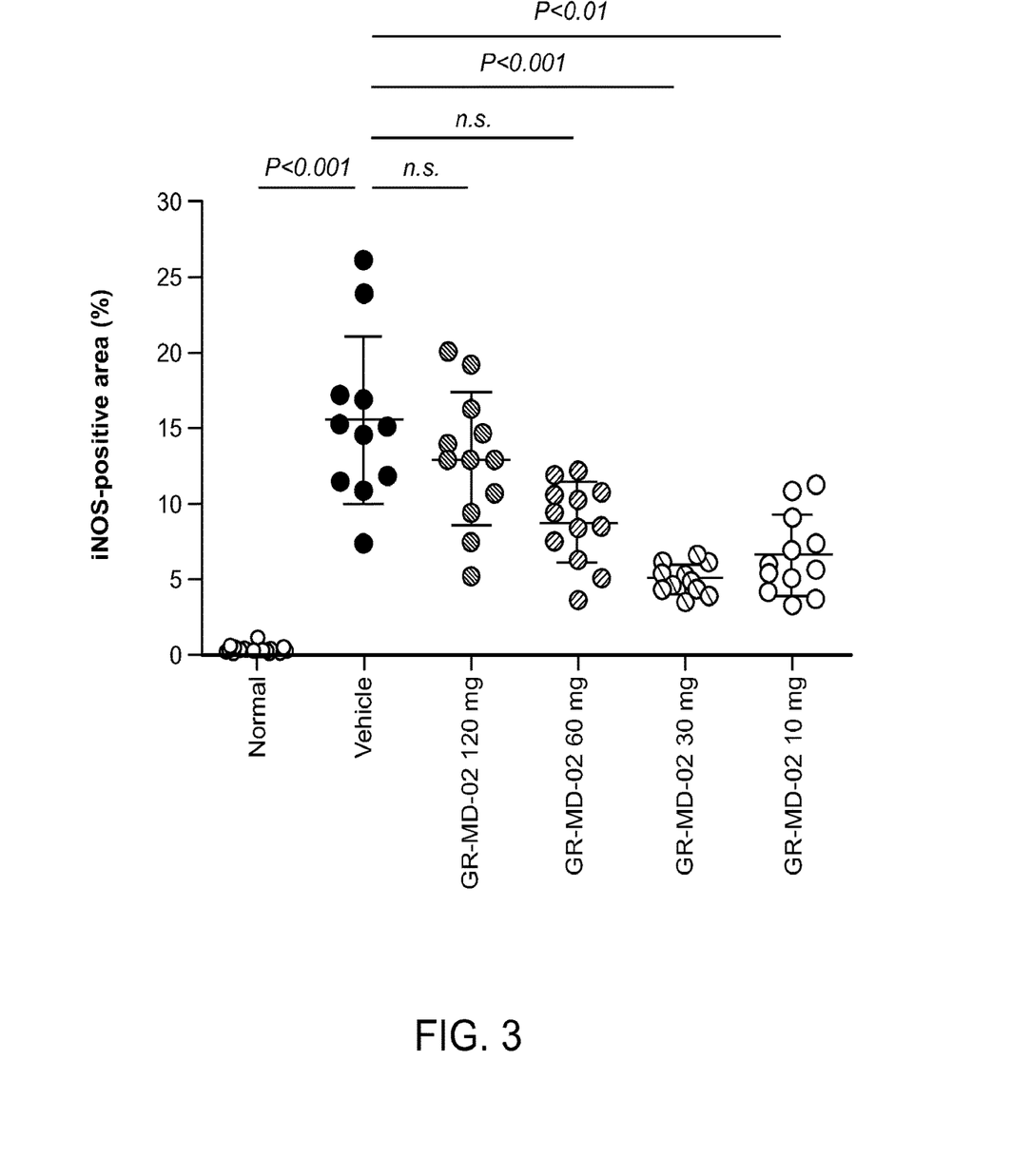
FIG. 3 shows digital morphometry of inducible nitric oxide synthase (iNOS) in liver tissue of experimental groups according to one embodiment.

FIG. 2 shows that the amount of iNOS detected in liver tissue was elevated in the vehicle-treated control livers over normal animals and reduced upon treatment with various doses of GR-MD-02 (10 mg/kg, 30 mg/kg, 60 mg/kg or 120 mg/kg). FIG. 3 shows the quantification of iNOS immunoreactivity which indicates that treatment with various once weekly doses of GR-MD-02 results in a reduction of iNOS immunoreactivity, with statistically significant reductions at doses of 30 mg/kg and 10 mg/kg once weekly.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:

1. A method comprising:
   administering to a subject in need thereof an effective dose of a composition,
   wherein the composition is for parenteral or enteral administration,
   wherein the composition comprises a galacto-rhamnogalacturonate in an acceptable pharmaceutical carrier,
   wherein the galacto-rhamnogalacturonate is a galactoarabino-rhamnogalacturonate, comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof, wherein the molar percent of the oligomers of 1,4-β-D-galactose residues and 1,5-α-L-arabinose residues is greater than 10% of the total carbohydrate molar content, and wherein the 1,4-β-D-galactose and 1,5-α-L-arabinose residues are present in a 2:1 to a 3:1 ratio,
   wherein the subject in need thereof has an autoimmune disease, a neurodegenerative disease, a cardiovascular disease, psoriasis, cutaneous and systemic lupus erythematosis, systemic sclerosis, or dermatitis,
   wherein the administering step results in a reduction of at least 10% of the expression of iNOS in a tissue affected by the disease.

2. The method of claim 1 wherein the galacto-rhamnogalacturonate has an average molecular weight ranging from 5 kDa to 55 kDa.

3. The method of claim 1 wherein the galacto-rhamnogalacturonate has an average molecular weight ranging from 2 kDa to 80 kDa.

4. The method of claim 1 wherein the galacto-rhamnogalacturonate has an average molecular weight ranging from 20 kDa to 70 kDa.

5. The method of claim 1 wherein the galacto-rhamnogalacturonate has an average molecular weight ranging from 2 kDa to 65 kDA.

6. The method of claim 1 wherein the galacto-rhamnogalacturonate has an average molecular weight ranging from 45 kDa to 65 kDa.

7. The method of claim 1 wherein the galacto-rhamnogalacturonate has an average molecular weight ranging from 2 kDa to 20 kDa.

8. The method of claim 1 wherein, in the step of administering, the galacto-rhamnogalacturonate is co-administered with an effective amount of a therapeutic agent.

9. The method of claim 8 wherein the therapeutic agent is one of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of the foregoing.

10. The method of claim 9 wherein the anti-oxidant compound comprises a water soluble Vitamin E preparation, mixed carotenoids, selenium or combinations thereof.

11. The method of claim 9 wherein the bile salt preparation comprises ursodeoxycholic acid, chenodeoxycholic acid of naturally occurring bile acids or bile acid salts, chenodeoxycholic acid of synthetic bile acids or bile acid salts or combinations thereof.

12. The method of claim 9 wherein the HMG-CoA reductase inhibitors comprises atorvastatin, simvastatin or combinations thereof.

13. The method of claim 9 wherein the galectin inhibitor comprises small organic inhibitors of galectin, monoclonal antibodies, RNA inhibitors, small binding peptides, protein inhibitors or combinations thereof.

14. The method of claim 9 wherein the antibody is an antibody against lysyl oxidase or an antibody against connective tissue growth factor.

* * * * *